US012106857B2

(12) United States Patent
Zhu et al.

(10) Patent No.: US 12,106,857 B2
(45) Date of Patent: Oct. 1, 2024

(54) COMPLEX CARE TOOL

(71) Applicant: Clover Health, Jersey City, NJ (US)

(72) Inventors: Kejia Zhu, San Francisco, CA (US); Brian Lucena, San Francisco, CA (US); Vincent La, San Francisco, CA (US); Laurie Jones, San Francisco, CA (US)

(73) Assignee: Clover Health, Jersey City, NJ (US)

( * ) Notice: Subject to any disclaimer, the term of this patent is extended or adjusted under 35 U.S.C. 154(b) by 227 days.

(21) Appl. No.: 16/215,158

(22) Filed: Dec. 10, 2018

(65) Prior Publication Data

US 2020/0185104 A1    Jun. 11, 2020

(51) Int. Cl.
*G16H 50/30* (2018.01)
*G16H 10/60* (2018.01)
*G16H 70/20* (2018.01)
*G16H 80/00* (2018.01)
*G06N 20/00* (2019.01)

(52) U.S. Cl.
CPC ............ *G16H 50/30* (2018.01); *G16H 10/60* (2018.01); *G16H 70/20* (2018.01); *G06N 20/00* (2019.01); *G16H 80/00* (2018.01)

(58) Field of Classification Search
CPC ........ G16H 10/60; G16H 50/30; G16H 70/20; G16H 80/00; G06N 20/00
See application file for complete search history.

(56) References Cited

U.S. PATENT DOCUMENTS

| | | | | |
|---|---|---|---|---|
| 5,486,999 A | * | 1/1996 | Mebane | G06Q 50/22 705/2 |
| 7,493,264 B1 | * | 2/2009 | Kelly | G06Q 10/06 705/2 |
| 8,095,380 B2 | * | 1/2012 | Wennberg | G06Q 10/10 705/2 |

(Continued)

OTHER PUBLICATIONS

Yang C., Delcher C., Shenkman E., Ranka S. (2017) "Machine Learning Approaches for Predicting High Utilizers in Health Care." In: Rojas I., Ortuño F. (eds) Bioinformatics and Biomedical Engineering. IWBBIO 2017. Lecture Notes in Computer Science, vol. 10209. Springer, Cham (Year: 2017).*

(Continued)

*Primary Examiner* — Mamon Obeid
*Assistant Examiner* — Chance L Smith
(74) *Attorney, Agent, or Firm* — Lee & Hayes, P.C.; Mike Merkelbach (57) ABSTRACT

Systems and methods for complex care tools are disclosed. For example, user data associated with users that have benefited from enrollment in a complex care program may be utilized to predict additional users that are also likely to benefit from enrollment. The presently disclosed systems and methods may determine reductions in cost profiles associated with enrolled users that exceed a reduction value, where the reduction value indicates the intended benefit of the complex care program has been achieved. The system may then associate user data of such users with the reduction value. As such, the system may utilize this data to predict additional users that are likely to benefit from enrollment. In this way, the system may engage such users to promote enrollment so that care costs may be reduced.

20 Claims, 5 Drawing Sheets

(56) References Cited

U.S. PATENT DOCUMENTS

| | | | |
|---|---|---|---|
| 2001/0020229 A1* | 9/2001 | Lash | G16H 50/70 705/3 |
| 2003/0060688 A1* | 3/2003 | Ciarniello | G06Q 40/08 600/300 |
| 2003/0195772 A1* | 10/2003 | Meek | G06Q 50/24 705/2 |
| 2008/0103369 A1* | 5/2008 | Fabius | G06F 19/328 600/300 |
| 2009/0240529 A1* | 9/2009 | Chess | G06Q 10/10 705/3 |
| 2013/0013336 A1 | 1/2013 | Wennberg | |
| 2013/0290005 A1* | 10/2013 | Vesto | G06Q 50/22 705/2 |
| 2014/0129257 A1* | 5/2014 | Ramachandran | G16H 40/20 705/3 |
| 2014/0257838 A1* | 9/2014 | Karra | G16H 20/00 705/2 |
| 2015/0039332 A1* | 2/2015 | Park | G06Q 10/0637 705/2 |
| 2015/0363569 A1* | 12/2015 | Ryan | G16H 20/00 705/3 |
| 2016/0125168 A1* | 5/2016 | Aagesen | G06F 19/3481 705/3 |
| 2016/0378927 A1* | 12/2016 | Merkin | G16H 40/63 705/2 |
| 2017/0011195 A1 | 1/2017 | Arshad et al. | |
| 2017/0083673 A1* | 3/2017 | Dawson, III | G16H 10/60 |
| 2017/0177808 A1* | 6/2017 | Irwin | G16H 40/63 |
| 2017/0220758 A1* | 8/2017 | Cox | G06F 19/3418 |
| 2017/0286622 A1 | 10/2017 | Cox et al. | |
| 2018/0068084 A1* | 3/2018 | Navani | G16H 20/00 |
| 2018/0114596 A1* | 4/2018 | Churchwell | G16H 40/63 |
| 2018/0181720 A1* | 6/2018 | Ensey | G16H 50/20 |

OTHER PUBLICATIONS

Mercer, Tim, et al. "The Highest Utilizers of Care: Individualized Care Plans to Coordinate Care, Improve Healthcare Service Utilization, and Reduce Costs at an Academic Tertiary Care Center." Jul. 2015. Journal of Hospital Medicine. vol. 10, No. 7. (Year: 2015).*

Yang, Chengliang et al. "Identifying High Health Care Utilizers Using Post-Regression Residual Analysis of Health Expenditures from a State Medicaid Program." AMIA . . . Annual Symposium proceedings. AMIA Symposium vol. 2017 1848-1857. Apr. 16, 2018 (Year: 2018).*

Morrison, R. Sean, et al. "Cost savings associated with US hospital palliative care consultation programs." Archives of internal medicine 168.16 (2008): 1783-1790. (Year: 2008).*

PCT Search Report and Written Opinion mailed on Feb. 5, 2020 for PCT Application No. PCT/US19/62268, a counterpart of U.S. Appl. No. 16/215,158, 9 pages.

* cited by examiner

```
┌─────────────────────────────────────────────────────────────────────────┐
│ Receive user data of users enrolled in the complex care program         │
│ including at least one of demographic information, medical histories,   │
│ or cost profiles                                                        │
│                              502                                        │
└─────────────────────────────────────────────────────────────────────────┘
                                  ↓
┌─────────────────────────────────────────────────────────────────────────┐
│ Determine, based at least in part on machine learning techniques, one   │
│ or more of the users that are associated with changes in the cost       │
│ profiles exceeding a reduction value                                    │
│                              504                                        │
└─────────────────────────────────────────────────────────────────────────┘
                                  ↓
┌─────────────────────────────────────────────────────────────────────────┐
│ Associate respective user data of the one or more users with the        │
│ reduction value                                                         │
│                              506                                        │
└─────────────────────────────────────────────────────────────────────────┘
                                  ↓
┌─────────────────────────────────────────────────────────────────────────┐
│ Receive user data associated with an additional user including at least │
│ one of additional demographic information, an additional medical        │
│ history, or an additional cost profile                                  │
│                              508                                        │
└─────────────────────────────────────────────────────────────────────────┘
                                  ↓
┌─────────────────────────────────────────────────────────────────────────┐
│ Determine that the additional user satisfies a requirement for          │
│ enrollment                                                              │
│                              510                                        │
└─────────────────────────────────────────────────────────────────────────┘
                                  ↓
┌─────────────────────────────────────────────────────────────────────────┐
│ Compare the respective user data and the additional user to determine   │
│ an association between the one or more users and the additional user    │
│                              512                                        │
└─────────────────────────────────────────────────────────────────────────┘
                                  ↓
┌─────────────────────────────────────────────────────────────────────────┐
│ Determine, based at least in part on the association and machine        │
│ learning techniques, that enrollment of the additional user in the      │
│ complex care program will result in a change in the additional cost     │
│ profile exceeding the reduction value                                   │
│                              514                                        │
└─────────────────────────────────────────────────────────────────────────┘
                                  ↓
┌─────────────────────────────────────────────────────────────────────────┐
│ Transmit a notification to a device associated with the additional user │
│ including an option to enroll in the complex care program               │
│                              516                                        │
└─────────────────────────────────────────────────────────────────────────┘
```

FIG. 5

COMPLEX CARE TOOL

BACKGROUND

Patients with high levels of resource utilization and/or with health conditions requiring close monitoring may benefit from enrollment in a care program tailored for patients with specialized needs. When a patient has specialized needs, they may require a program designed to manage care across medical conditions and associated specialists. If the patient does not have the appropriate care, they may be associated with high levels of resource utilization (e.g., emergency care, excess prescriptions, etc.) due to a lack of prolonged care strategies, thus leading to increased medical care expenses for both the individual and the insurance provider. Described herein are improvements in technology and solutions to technical problems that can be used to, among other things, assist with predicting users that may benefit from enrollment in a complex care program.

BRIEF DESCRIPTION OF THE DRAWINGS

The detailed description is set forth below with reference to the accompanying figures. In the figures, the left-most digit(s) of a reference number identifies the figure in which the reference number first appears. The use of the same reference numbers in different figures indicates similar or identical items. The systems depicted in the accompanying figures are not to scale and components within the figures may be depicted not to scale with each other.

DETAILED DESCRIPTION

Systems and methods associated with complex care tools are described herein. For example, certain users with specialized health care needs may benefit from enrollment in complex care programs tailored for certain medical statuses and/or conditions. In some instances, characteristics such as disease status, demographic information, medical history, and other information may be associated with users that would benefit from complex care. With conventional systems, users may be inaccurately targeted for enrollment based on erroneous indicators (e.g., presumptions based simply on old age, high-risk diseases, etc.). As a result, such users may not benefit from complex care or may be unresponsive to engagement encouraging enrollment, thus negating the intended effects of care programs such as reduced resource utilization, improved health of users, reduced cost profiles, etc. In addition, conventionally, the type of engagement used in interacting with a targeted user may be a generic type and may not be effective for particular users (e.g., a text may be sent to a user who doesn't have a mobile device). Thus, the engagement process may be ineffective in achieving enrollment of the user in the complex care program. As such, the need arises to implement systems and methods for complex care tools that will allow a system to accurately predict users that will benefit from enrollment in a complex care program and determine an effective engagement process that will result in timely enrollment. In this way, the system may take measures to enroll users in programs that will result in reduced cost profiles and improved health.

The present invention is directed to systems and methods that employ predictive techniques and machine learning models to accurately predict that a user will benefit from enrollment in a complex care program and, further, identify a type of care program and/or a type of engagement that will be most effective in achieving enrollment of the user. For example, the system may access, or receive, user data associated with one or more users, such as demographic information, a medical history, or a cost profile associated with the user. The user data may include such information as medical conditions, resource utilization, physical characteristics (e.g., age, ethnicity, etc.), provider information, etc. that may be obtained from a user database, provided by the user, and/or accessed from one or more medical databases. In addition, the system may identify, or access, requirements associated with a complex care program. For example, the requirements may include age limitations, applicable health conditions, cost utilization thresholds, etc. In this way, the system may utilize the user information to determine if a user is a candidate for enrollment in a complex care. Further, in some embodiments, the system may determine if a user is a candidate for enrollment in a specific complex care program such as, for example, a complex care program geared for the elderly or users with a certain health condition.

In examples, based on determining that the user satisfies the complex care program requirements, and thus is a candidate for enrollment, the system may transmit a notification to the user regarding enrollment in the complex care program. For example, the system may send a notification to a user device associated with the user with an option to enroll in the program, receive additional information regarding the program, schedule an informational consultation, etc. In particular, the notification may cause the user device to initiate an application residing on the device and cause the option to be displayed.

In addition, the system may determine a type of enrollment that is most efficient in resulting in enrollment of the user in the complex care program. For example, based on user feedback, the system may determine that a type of communication (e.g., a text, email, phone call, etc.) is most effective in engaging the user and resulting in enrollment. Further, the system may determine the type of content provided in the notification that is most effective in resulting in enrollment. For example, the system may determine that providing multiple options in the notification, such as an option to enroll along with an option to schedule a consultation, is most effective in engaging the user and resulting in enrollment.

Additionally, the system may receive an indication that the user has interacted with the notification and/or that the user has selected the option to enroll in the complex care program. For example, the system may receive an indication that the user has selected the option to enroll in the complex care program. Based at least in part on the indication that the user has selected the option to enroll, the system may cause the user to be enrolled in the complex care program.

In examples, the system may determine a change in the user's cost profile. In particular, the system may determine that the change in the cost profile exceeds a reduction value. For example, the system may determine that the cost profile has been reduced by a certain value. The reduction value may be a predetermined value and/or may be determined by machine learning techniques. The reduction value may be associated with an intended benefit of enrollment in the complex care program. For example, the reduction value may indicate that the cost profile has been reduced by a large enough value or percentage to determine that the complex care program has been effective and/or beneficial to the user. As a result of the change in the cost profile exceeding the reduction value, the system may associate the user data with the reduction value. For example, the system may associate the user data with a reduction in value indicating an effectiveness of the complex care program.

The system may utilize this user data, along with machine learning techniques, to predict whether additional users will benefit from enrollment in the complex care program. For example, the system may receive user data associated with an additional user. The system may determine that the additional user is also a candidate for enrollment in the complex care program. The system may then compare the user data from the first user with that of the additional user to determine if there is an associate between the first user and the second user. Based at least in part on determining an association, along with utilizing machine learning techniques, the system may predict, or determine, that enrollment of the additional user in the complex care program will result in a change to a cost profile of the additional user that also exceeds the reduction value. As a result, the system may send a notification to a device associated with the additional user with an option to enroll in the complex care program.

In the examples described herein, the system may perform similar operations regarding multiple users. For example, the system may receive and/or access user information regarding a multitude of users. Utilizing the user information, the system may determine one or more users associated with changes in additional cost profiles that exceed the reduction value. The system may then associate user data associated with the one or more users with the reduction value. From this information, the system may implement one or more machine learning techniques to predict, or determine, whether additional users may benefit from enrollment in the complex care program (e.g., have a reduced cost profile exceeding the reduction value).

Additionally, or alternatively, the systems and methods described herein may be configured to determine, based at least in part on the selection indications and enrollment data, and utilizing one or more machine learning techniques, a type of notification and/or the type of notification content that is most effective in engaging users and/or the type of program that would be most beneficial. For example, indications of user selections may indicate that a user, or multiple users, has received notifications but has not interacted with the notification and/or has not enrolled in the complex care program. As such, the system may determine that the user(s) should not receive future notifications and/or that the user(s) are not responsive to a certain type of notification. Alternatively, the selection indications may indicate that the user(s) have interacted with the reminder and should receive future reminders and/or has interacted with a certain type of notification (e.g., an email, text, phone call, etc.). In addition, the selection indications may be compared with a certain threshold of effectiveness. For example, if the user(s) have not interacted with a certain percentage of notifications, the user(s) may or may not receive future notifications. In addition, the selection indications may indicate that the user(s) have interacted with some types of notifications and/or content (e.g., a link to sign up, a link to schedule an informational consultation, etc.) and not others. As such, the system may determine that a type of notification and/or content is more effective in engaging the user(s) and resulting in enrollment of the user(s) and may only transmit that type of notification and/or content to the user(s) in the future.

By using predictive learning techniques, the system may proactively target users who will benefit from enrollment in a complex care program and ensure that effective notifications are sent that will ensure user engagement. In this way, accessible user information can be utilized to increase effectiveness of complex care programs and reduce elevated health care costs. In contrast to conventional techniques involving human decision-makers, the techniques described herein allow the system to make real-time, automated, and/or unbiased predictions of users who will experience a reduced cost profile from enrollment and/or determinations regarding a type of complex care program, a type of notification, and/or notification content that will be most effective for the user, with improved speed and accuracy.

Additionally, the rules, algorithms, and various techniques described herein are designed to be implemented utilizing computerized components, as described herein, and could not be performed by human decision-makers while achieving the same results. In addition, the results achieved from the combination of steps performed and/or data points considered, allow the algorithms and machine learning techniques to constantly improve the functioning of the computerized components. For example, by more accurately predicting users who will benefit from enrollment in a complex care program, based on a specific method and/or data points, the system may prevent both the sending of ineffective notifications, as well as the enrollment of users in complex care programs who will not achieve the intended benefits/results. Thus, as a result of determining/predicting which users to target, the type of notification to send, and/or the content of the notification, the system may implement more effective engagement techniques. More specifically, since the system can determine/predict characteristics of notifications with greater accuracy, to increase efficacy of the reminders, as well as more accurately determine/predict users who will benefit from the complex care program, the computer may utilize less resources sending extraneous reminders and enrolling users who will not benefit from enrollment. In addition, by refining the process using machine learning techniques and iterative algorithms, the computer may increase efficiency as more data points are collected.

Also, the user alerts, or notifications, described herein are time-sensitive in nature and configured to be transmitted to a user device in real-time for display on a user device via an interface, application program, etc. In this way, the reminders will cause the user device to display the reminder in a timely manner and increase the likelihood that the user will interact with the reminder and enroll in the complex care program.

The present disclosure provides an overall understanding of the principles of the structure, function, manufacture, and use of the systems and methods disclosed herein. One or more examples of the present disclosure are illustrated in the accompanying drawings. Those of ordinary skill in the art will understand that the systems and methods specifically described herein and illustrated in the accompanying drawings are non-limiting embodiments. The features illustrated or described in connection with one embodiment may be combined with the features of other embodiments, including as between systems and methods. Such modifications and variations are intended to be included within the scope of the appended claims.

Additional details are described below with reference to several example embodiments.

Figure 1:
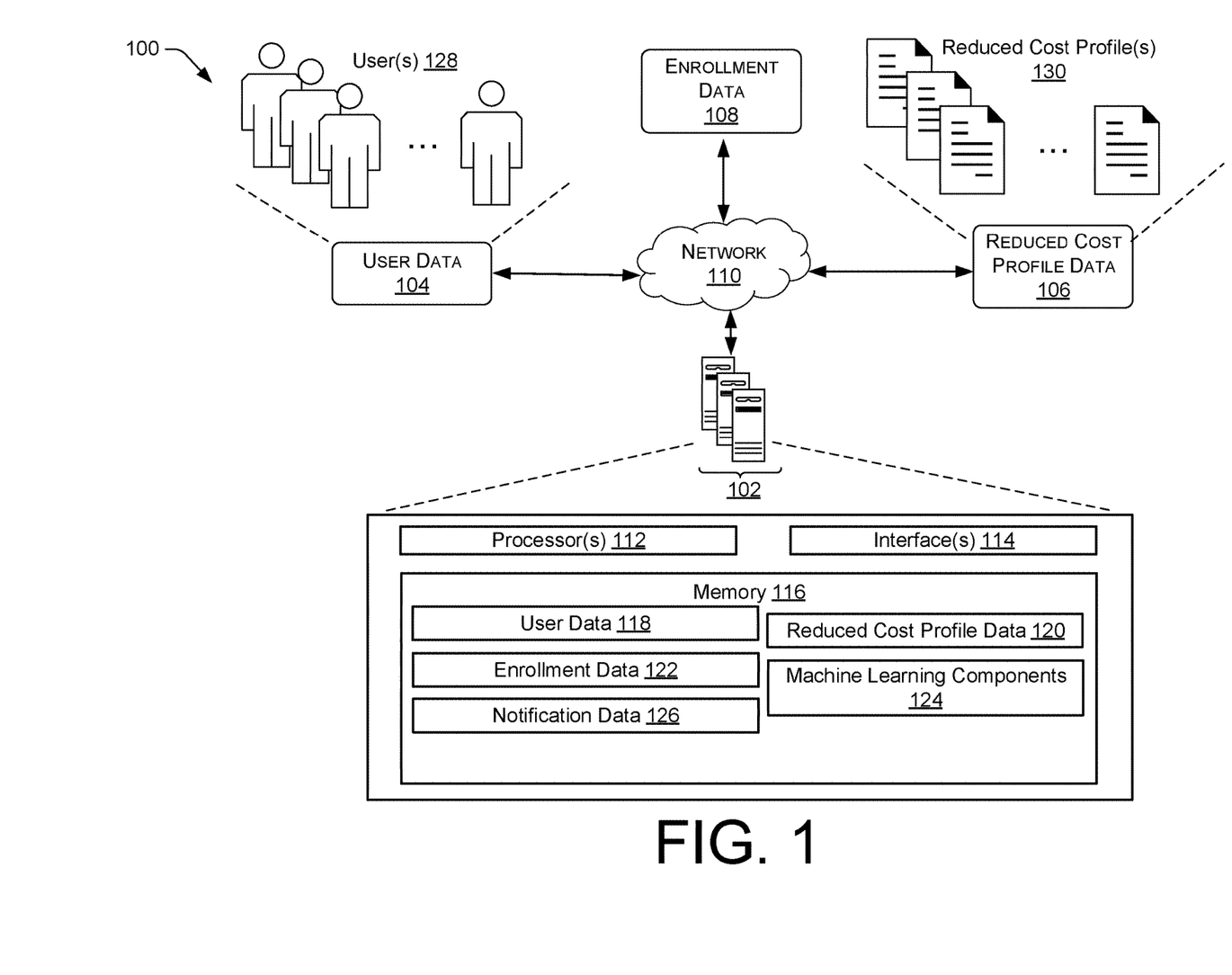
FIG. 1 illustrates a schematic diagram of an example environment for complex care tools.

FIG. 1 illustrates a schematic diagram of an example environment 100 for complex care tools. The environment 100 may include, for example, a system 102 configured to receive user information including user data 104, reduced cost profile data 106, and enrollment data 108 via a network 110. It should be understood that, while FIG. 1 depicts one system, the environment 100 may include any number of systems configured to operate independently and/or in combination and configured to communicate with each other via the network 110. It should also be understood that while the object is described as a "system," the object may be considered a device. The components of the system 102 will be described in detail below.

For example, the system 102 may include one or more processors 112, one or more network interfaces 114, and memory 116. The memory 116 may include one or more components, such as, for example, a user data component 118, a reduced cost profile data component 120, an enrollment data component 122, a notification data component 126, and one or more machine learning components 124. At least some of the components of the memory 116 will be described below.

The user data component 118 may be configured to store and/or access data associated with the system 102. The data may be any data associated with the system 102. In examples, the data may be the user data 104. For example, the user data 104 may be data associated with multiple users 128 utilizing the system 102. In particular, the user data 104 may include data associated with at least some of the users 128 including, but not limited to, demographic data, medical history data (e.g., disease status, lab results, etc.), cost profile data (e.g., resource utilization, cost to insure, general costs associated with care of the user without enrollment, etc.), and/or any other data provided by the users 128 or able to be obtained from medical records associated with the users 128.

In examples, the user data 104 may be transmitted to the system 102 via the network 110 from one of the users 128 or a third-party system. In other examples, the user data 104 may be accessed from an external storage component, such as a database or cloud-based storage device, by the system 102. The user data 104 may be utilized by the system 102 to predict, or determine, users that will benefit from enrollment in a complex care program, as described herein.

The reduced cost profile data component 120 may be configured to store and/or access additional data associated with the system 102. In examples, the additional data may be the reduced cost profile data 106. For example, the reduced cost profile data 106 may include data associated with one or more reduced cost profiles 130 associated with users 128 that have benefited for enrollment in the complex care program. In particular, the reduced cost profiles 130 may include information associated with cost profiles that have been reduced by a certain reduction value as a result of enrollment in the complex care program. The reduction value may indicate a numerical value or a percentage value by which the cost profiles have been reduced. The reduction value may be a predetermined value, or a value determined by the system and the machine learning components 124, as being associated with the intended effectiveness of the complex care program (e.g., when the cost profile of a user has been reduced by a value of 40%, this indicates that enrollment of the user in the complex care program has been effective and/or beneficial).

In examples, the reduced cost profile data 106 may be transmitted to the system 102 via the network 110 and/or may be accessed from an external storage component, such as a database or cloud-based storage device, by the system 102. reduced cost profile data 106 may be utilized by the system 102 to determine user data 104 associated with the reduced cost profiles 130 for use in predicting whether an additional user may benefit from enrollment in the complex care program. For example, the reduced cost profile data 106 may include, but not be limited to, data associated with the reduced cost profiles 130 including, but not limited to, daily/monthly/yearly resource utilization, benefits paid out for health care, prescription benefits, etc.

In examples, the enrollment data component 122 may be configured to store and/or access additional data associated with the system 102. In examples, the additional data may be the enrollment data 108. For example, the enrollment data 108 may include data indicating users that are currently enrolled in a complex care program, requirements associated with the complex care program, and/or requirements associated with individual care programs of the complex care program. For example, the enrollment data 108 may include data associated with users enrolled in the complex care program such as identification information (e.g., name, birthday, social security number, etc.), a date of enrollment, and/or an enrollment method (e.g., via a website, over the phone, etc.). In additional the enrollment data 108 may include enrollment requirements that must be satisfied before a user may be a candidate for enrollment. For example, the enrollment data 108 may include requirements for the complex care program and/or individual care programs such as age, disease status, resource utilization, cost profile levels, etc. In this way, the system 102 may utilize the enrollment data 108, along with the user data 104, to determine if a user is a candidate for enrollment and/or which program the user qualifies for.

Further, the memory 116 may store one or more machine learning components 124 configured to train, or create, one or more complex care tools. As described in more detail in FIG. 2, the machine learning component(s) 124 may receive, such as during a user onboarding process and/or a set-up process, training data that is utilized to train, generate, or otherwise determine the complex care tools models. For example, the machine learning component(s) 124 may execute one or more algorithms (e.g., decision trees, artificial neural networks, association rule learning, or any other machine learning algorithm) to train the complex care tools models that determine, based at least in part on various data, whether a user will benefit from enrollment in a complex care program (e.g., experience a cost profile reduction by at least the reduction value), a type of care program that will be most beneficial (e.g., a program designed for a specific disease or the use of certain specialists), an effectiveness of transmitting a notification to enable enrollment, and/or an effectiveness associated with various aspects of the type of notification such as content, time, date, and/or means of communicating the notification.

Information from stored and/or accessible data may be extracted from one or more databases, such as for example the user data component 118, reduced cost profile data component 120, and/or enrollment data component 122, and may be utilized to predict trends and behavior patterns. The predictive analytic techniques may be utilized to determine associations and/or relationships between explanatory variables and predicted variables from past occurrences and utilizing these variables to predict the unknown outcome. The predictive analytic techniques may include defining the outcome and data sets used to predict the outcome. Then, data may be collected and/or accessed to be used for analysis.

For example, the machine learning components 124 may access data from the user data component 118, the reduced cost profile data component 120, and/or the enrollment data component 122 relating to a particular user. More specifically, the machine learning components 124 may access enrollment data 108 indicating whether the user is a candidate for enrollment or whether the user is already enrolled in a complex care program, user data 104 associated with the user, and/or a reduced cost profile 130 associated with the user and indicating whether the user has experienced a reduction in an associated cost profile by at least the reduction value as a result of enrollment. From this information, the machine learning components 124 may utilize the complex care tools model(s) to determine user data 104, or a combination of user data 104, associated with users that have experienced a reduced cost profile from enrollment in the complex care program and/or the type, content, delivery method, etc. associated with a notification to enroll that the user has, or is likely to, respond to. Utilizing this information, the system 102 can identify users that would likewise benefit from enrollment in the complex care program. In addition, the system 102 may identify characteristics of the user data not commonly associated with users who are likely to benefit from enrollment and/or that, when taken individually, do not indicate a user likely to benefit from enrollment but, when taken in combination, identify that the user is, in fact, likely to benefit.

In examples, the notification data component 126 may be configured to generate and transmit notification(s) including an option to enroll in the complex care program, and receive user responses associated with the notification(s). For example, the notification data component 126 may receive a signal from the machine learning components 124 to cause the notification data component 126 to generate a notification for a user. As described above, when the machine learning components 124 determine that a user is likely to experience a reduced cost profile from enrollment, the machine learning components 124 may transmit a signal to the notification data component 126 to cause the notification data component 126 to generate a notification including an option to enroll in the complex care program and/or an individual care program. The notification may include, but not be limited to, a notification for display on a device associated with the user, a communication to caregiver or facility associated with the user (e.g., as indicated by the user data 104), etc. Additionally, in examples, the notification or communication may include an option to access additional information regarding the suggested program(s), a link to an enrollment platform, an option to schedule an additional notification, etc.

Additionally, the notification(s) may be configured to cause an application residing on the user device to be activated and display the notification to the user. For example, the notification(s) may cause a device application to activate and display the enrollment option and/or generate an interactive user interface including the enrollment option, selectable elements, interactive links, etc. In addition, due to the need to enroll the user as soon as possible to maximize the cost benefit, the reminder alert(s) may be time-sensitive in nature. For example, the notification(s) may be configured to be transmitted to the user device in real-time as the user's likelihood to enroll may be triggered by a recent event and/or a condition the user is currently experiencing (e.g., an emergency room visit, access to the enrollment platform, etc.). For example, the notification data component 126 may determine, through predetermined parameters or machine learning techniques, that the notification must be transmitted during as a result of a triggering event, during a certain time of day (e.g., after working hours), and/or at least a certain amount of days/hours/minutes after the event in order to increase the effectiveness of the notification.

In examples, the notification data component 126 may utilize one or more of the user data 104, the enrollment data 108, the reduced cost profile data 106, and/or the machine learning components 124 to determine the most effective type of notification for user(s) and/or when and how it is transmitted. For example, the notification data component 126 may access the user data 104, via the user data component 118, the enrollment data 108, via the enrollment data component 122, and/or the reduced cost profile data 106, via the reduced cost profile data component 120, to determine one or more aspects of the notification. For example, the user data 104 may indicate that the user has a mobile device and/or does not subscribe to email. In this instance, the notification data component 126 may determine that the notification should include a communication via mobile phone call and/or text message. In yet another example, the one or more machine learning components 124 may provide data indicating that, based at least in part on historical data, the user is more likely to respond to a notification including an option to view additional data regarding the complex care program. In this instance, the notification data component 126 may determine that the notification should only an interactive link to an external website outlining the program specifications.

In examples, the notification data component 126 may be configured to receive, via the network 110, and/or store data relating to, any user interaction with the transmitted notification. For example, the notification data component 126 may be configured to receive an indication that at least one of a user interaction with a notification and/or a lack of interaction with the notification. In addition, the indication may further include the type of user interaction received, such as a selection, a dismissal, etc. associated with the type and/or content of the notification. The one or more indications may be stored, either locally or remotely, within a database for access by the system 102.

As used herein, a processor, such as processor(s) 112, may include multiple processors and/or a processor having multiple cores. Further, the processors may comprise one or more cores of different types. For example, the processors may include application processor units, graphic processing units, and so forth. In one implementation, the processor may comprise a microcontroller and/or a microprocessor. The processor(s) 112 may include a graphics processing unit (GPU), a microprocessor, a digital signal processor or other processing units or components known in the art. Alternatively, or in addition, the functionally described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), etc. Additionally, at least some of the processor(s) 112 may possess its own local memory, which also may store program components, program data, and/or one or more operating systems.

The memory 116 may include volatile and nonvolatile memory, removable and non-removable media implemented in any method or technology for storage of information, such as computer-readable instructions, data structures, program component, or other data. Such memory 116 includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, RAID storage systems, or any other medium which can be used to store the desired information and which can be accessed by a computing device. The memory 116 may be implemented as computer-readable storage media ("CRSM"), which may be any available physical media accessible by the processor(s) 112 to execute instructions stored on the memory 116. In one basic implementation, CRSM may include random access memory ("RAM") and Flash memory. In other implementations, CRSM may include, but is not limited to, read-only memory ("ROM"), electrically erasable programmable read-only memory ("EEPROM"), or any other tangible medium which can be used to store the desired information and which can be accessed by the processor(s).

Further, functional components may be stored in the respective memories, or the same functionality may alternatively be implemented in hardware, firmware, application specific integrated circuits, field programmable gate arrays, or as a system on a chip (SoC). In addition, while not illustrated, each respective memory, such as memory 116, discussed herein may include at least one operating system (OS) component that is configured to manage hardware resource devices such as the network interface(s), the I/O devices of the respective apparatuses, and so forth, and provide various services to applications or components executing on the processors. Such OS component may implement a variant of the FreeBSD® operating system as promulgated by the FreeBSD Project; other UNIX® or UNIX-like variants; a variation of the Linux® operating system as promulgated by Linus Torvalds; the FireOS operating system from Amazon.com Inc. of Seattle, Washington, USA; the Windows® operating system from Microsoft Corporation of Redmond, Washington, USA; LynxOS® as promulgated by Lynx® Software Technologies, Inc. of San Jose, California; Operating System Embedded (Enea® OSE) as promulgated by ENEAR AB of Sweden; and so forth.

The network interface(s) 114 may enable communications between the components and/or devices shown in environment 100 and/or with one or more other remote systems, as well as other networked devices. Such network interface(s) 114 may include one or more network interface controllers (NICs) or other types of transceiver devices to send and receive communications over the network 110.

For instance, at least some of the network interface(s) 114 may include a personal area network (PAN) component to enable communications over one or more short-range wireless communication channels. For instance, the PAN component may enable communications compliant with at least one of the following standards IEEE 802.15.4 (ZigBee®), IEEE 802.15.1 (Bluetooth®), IEEE 802.11 (WiFi), or any other PAN communication protocol. Furthermore, at least some of the network interface(s) 114 may include a wide area network (WAN) component to enable communication over a wide area network.

Figure 2:
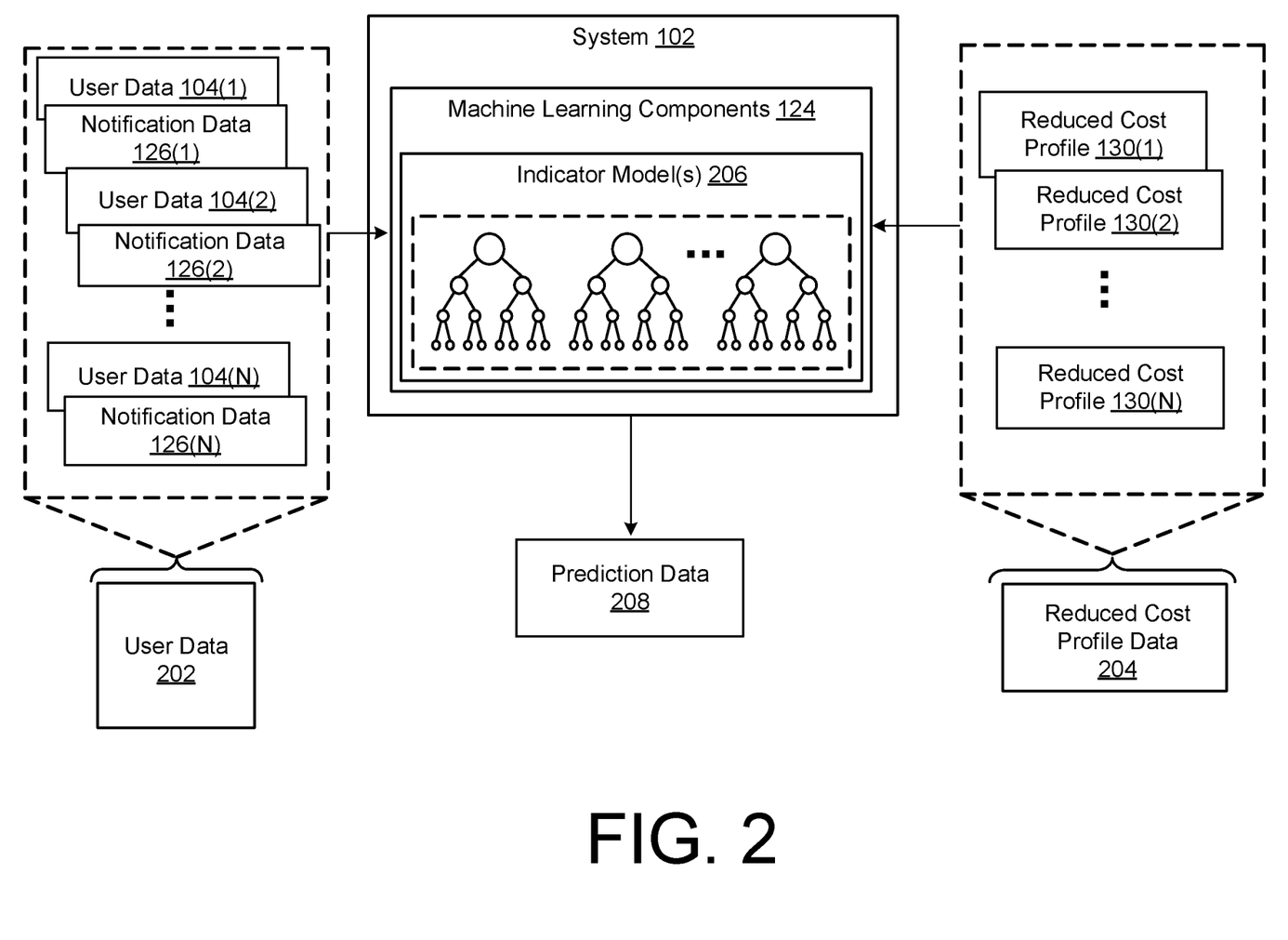
FIG. 2 illustrates an example of generating and/or training a model of complex care tools to identify one or more users that would benefit from enrollment in a complex care program.

FIG. 2 illustrates an example of generating or training a model of complex care tools to identify one or more users that would benefit from enrollment in a complex care program. For example, the one or more machine learning components 124 of computing device(s) 102, depicted and described in FIG. 1, may receive and/or determine user data 202. In examples, the user data 202 may include user data associated with multiple users (e.g., user data 104(1), notification data 126(1), user data 104(2), notification data 126(2) . . . user data 104(N), notification data 126(N)) of the system 102. In addition, the one or more machine learning components 124, may receive and/or determine reduced cost profile data 204. In examples, the reduced cost profile data 204 may include reduced cost profile(s) (e.g., reduced cost profile 130(1), reduced cost profile 130(2), . . . reduced cost profile 130(N)).

The user data 202 and/or reduced cost profile data 204 may be utilized by the one or more machine learning components 124 configured to execute one or more machine learning algorithms to train one or more indicator model(s) 206 to determine one or more users that will benefit from enrollment in a complex care program. In addition, the one or more machine learning components 124 may be configured to identify characteristics of the user data 202, alone or in combination, that are associated with users that will benefit from enrollment and/or respond to notifications with enrollment options, and/or the type, content, delivery method, etc. of the notification(s) including an enrollment option that the user has, or is likely to, respond to. Although the indicator model(s) 206 is illustrated as a decision-tree trained model, the machine learning component(s) 24 may execute any type of supervised learning algorithms (e.g., nearest neighbor, Naïve Bayes, Neural Networks, unsupervised learning algorithms, semi-supervised learning algorithms, reinforcement learning algorithms, and so forth).

In examples, the user information 202 may include various user data 104 associated with users. For example, the user data 104 may include data associated with users such as identification information (e.g., name, social security number, etc.), demographic information, a medical history (e.g., medical test results, disease status, physician information, etc.), or a cost profile of a user (e.g., resource utilization, benefits paid out for office visits and/or prescription medication, etc.), and/or any other data provided by users or able to be obtained from medical records associated with the users. Additionally, the user information 202 may include various notification data 126 associated with notifications that have, or will be, generated and transmitted to users. For example, the notification data 126 may include user response(s) to transmitted notifications including option(s) to enroll in the complex care program. The notification data 126 may include an of a user interaction with a notification, a lack of interaction with the notification, and/or the type of user interaction received, such as a selection, a dismissal, etc. associated with the type and/or content of the notification. The notification data 126 may also include data such as the type of notification generated and/or the content of the notification.

Further, the reduced cost profile data 204 may include various reduced cost profile(s) 130 associated with users that have benefited from enrollment in the complex care program. In particular, the cost profile(s) 130 may include cost profile(s) that have experienced a reduction in a cost profile by at least a reduction value, where the reduction value may include a predetermine value programmed into the system and/or a reduction value that has been determined by the machine learning components 124 as achieving the intended benefit of the complex care program. In other words, the machine learning components 124 may determine that a reduction in a cost profile 130 by 40% is associated with satisfying the intended benefit of the complex care program. The cost profile(s) 130 may include information associated with a user's resource utilization, benefits paid out to care providers and/or for prescription medications, etc.

In examples, the machine learning component(s) 124 may train the indicator model(s) 206 based at least in part on user data 202 and reduced cost profile data 204 received over time. For example, the indicator model(s) 206 may be trained to determine prediction data 208 including aspects of the user data 202 and/or one or more combinations of the aspects of the user data 202 associated with users who benefit from enrollment. For example, the indicator model(s) 206 may utilize user data 202 and reduced cost profile data 204 over time to learn that users benefitting from enrollment in the complex care program are associated with one or more characteristics and/or combinations of characteristics of the user data 104. As a specific example, the indicator model(s) 206 may be trained, over time, to determine that users who have diabetes benefit from enrollment. As another specific example, the indicator model(s) 206 may be trained, over time, to determine that users possessing the combination of being over the age of 50 and having an early stage chronic disease will benefit from enrollment. The one or more characteristics of the user data 104, alone or in combination, associated with users benefitting from enrollment may be determined and stored as predictive user(s) data 208.

In this way, when it is determined that another user is a candidate for enrollment, the system 102 may utilize the predictive user(s) data 208 to predict if the user will likewise benefit from enrollment and experience a reduction in their cost profile by at least the reduction value. In particular, the system 102 may analyze the user data 104 of the additional user to determine an association between the user data 104 and the prediction data 208. If an association exists, the system 102 may predict that the additional user will benefit from enrollment. In addition, the system 102 may not identify the particular user data characteristics determined in the prediction data 208, but may simply store the prediction data 208 and utilize this information to make predictions for additional users.

Additionally, in examples, the indicator model(s) 206 may be trained, over time, to determine the type, content, and means of notifying users that is most effective in engaging users and resulting in enrollment. For example, the indicator model(s) 206, utilizing the user information 202 and reduced cost profile data 204, may determine that users are more likely to enroll in a complex care program if they receive a text message, in lieu of a phone call. As an example, based at least in part on the user data 202, including user data 104 and notification data 126, the indicator model(s) 206 may determine that users under the age of 25 are more likely to interact with, and/or enroll via the notification, if the notification is transmitted via text. Alternatively, or in addition to, the indicator model(s) 206 may determine that a certain type of notification is most effective among a current user group and may generate all future reminders accordingly. As such, the indicator model(s) 206 may be able to provide information to the system 102 to allow generation and transmission of intelligent, and targeted notifications to users, thereby increasing the likelihood that a user will interact with the notification and/or that the notification will result in enrollment of the user in the complex care program.

Figure 3:
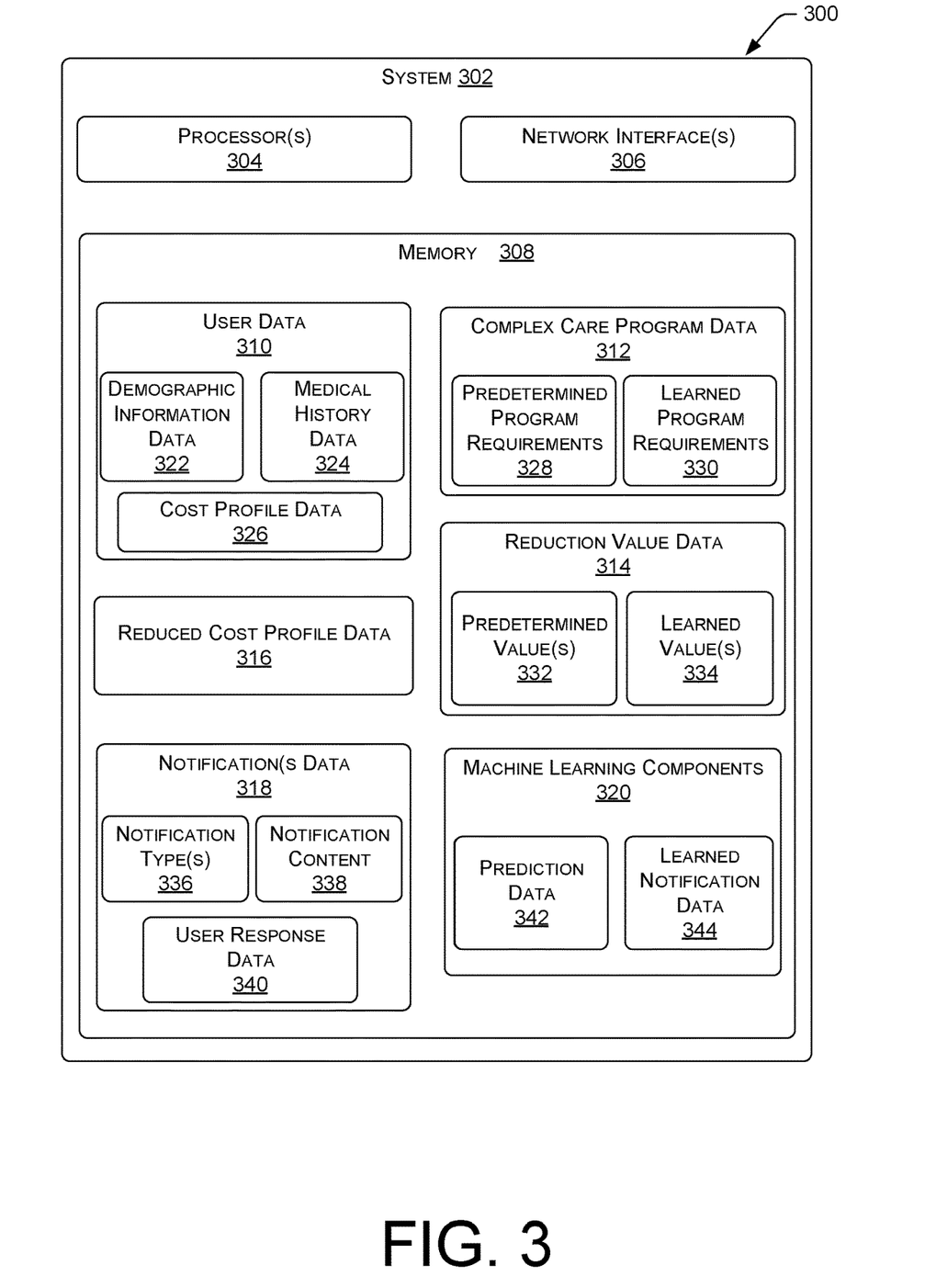
FIG. 3 illustrates a functional block diagram of an example system for complex care tools.

FIG. 3 illustrates a functional block diagram 300 of an example system 302 for complex care tools. The system 302 may perform the same or similar functions as the system 102 described in FIG. 1. The system 302 may comprise processor(s) 304 that are operatively connected to network interface(s) 306 and a memory 308.

The memory 308 may store user data 310, complex care program data 312, reduction value data 314, reduced cost profile data 316, notification(s) data 318, and/or machine learning components 320. In examples, the user data 310 may include both user provided data and user data accessed from a third-party system or database. For example, system 302 may access, via the processor(s) 304, a third-party databased or healthcare system and obtain user information associated with one or more users. In examples, the user data 310 may include demographic information data 322, such as age, gender, location, etc. The user data 310 may also include medical history data 324, such as disease status, lab results, physicians providing care, hospital records, etc. Further, the user data may include cost profile data 326, such as resource utilization, benefits paid out, average yearly cost of care, extended care costs, etc.

In examples, the memory 308 may store complex care program data 312 including predetermined program requirements 328 and learned program requirements 330. The complex care program data 312 may include requirements for the complex care program and/or individual care programs within the complex care program. For example, the complex care program data 312 may include demographic requirements, such as age and/or gender, disease requirements, such as a type of disease the program is designed to benefit/care for, care physicians that are recommended for members of each program, etc. The complex care program data 312 may include predetermined program requirements 328, such as those that have been predetermined and/or pre-programmed into the system 302 by system administrators, program directors, and/or any other party authorized to dictate requirements of the complex care program.

Alternatively, or in addition to, the complex care program data 312 may include learned program requirements 330, where the program requirements have been determined utilizing the machine learning components 320. For example, the machine learning components 320 may implement one or more predictive algorithms and/or application programming interfaces (APIs) to calculate the learned program requirements 330 based at least in part on the user data 310, reduction value data 314, and/or reduced cost profile data 316. For example, utilizing historical data of the system 302, the machine learning components 320 may determine that users having certain characteristics, such as certain diseases, ages, etc. benefit most (e.g., have a high level of cost profile reduction by at least the reduction value) from the complex care program and/or an individual care program. Utilizing this information, the machine learning components 320 may determine which learned program requirements 330 are best suited for a particular care program.

In examples, the memory 308 may store reduction value data 314 including predetermined value(s) 332 and learned value(s) 334. For example, the reduction value data 314 may include values by which a cost profile must be reduced to indicate an effectiveness of a user's enrollment in the complex care program. The predetermined value(s) 332 may include values that have been previously determined by the system 302 or pre-programmed into the system 302. For example, it may be determined that a predetermined value 332 of a 40% reduction in a user's cost profile indicates the intended benefit of enrollment. Alternatively, or in addition to, the system 302 may determine, by the machine learning components 320, that learned value(s) 334 are associated with a benefit of enrollment. For example, the machine learning components 320 may determine, via historical data and past iterations, that a certain reduction value is associated with the intended benefit of enrollment. The reduction value data 314 may be associated with the complex care program and/or individual care programs of the complex care program (e.g., each care program may be associated with a different reduction value that indicates that the benefit of the specific program has been achieved).

In embodiments, the memory 308 may store reduced cost profile data 316 including reduced cost profiles of users. The reduced cost profile data 316 may include cost profiles associated with users that have benefited from enrollment in the complex care program. For example, the reduced cost profile data 316 may utilize the reduction value data 314 to determine if an enrolled user's cost profile has been reduced by at least the reduction value associated with the complex care program, and/or the reduction value associated with the individual care program. If the system 302 determines that the cost profile has been reduced by the required reduction value, the system 302 may store the cost profile data in the reduced cost profile data 316. In addition, the reduced cost profile data 316 may include one or more aspects of the user data 310 associated with the reduced cost profile. In this way, the system 302 may access the reduced cost profile data 316 and correlate the reduced cost profiles with the associated user data 310.

In examples, the reduced cost profile data 316 may be determined as a result of monitoring and/or a triggering event. For example, in response to the user being enrolled in the complex care program and/or one or more individual care programs, the system 302 may continually monitor the cost profile data 326 in order to detect changes. Alternatively, or in addition to, the system 302 may analyze the cost profile in response to a triggering event in order to see if any changes have been deducted. For example, in response to a triggering event, such as a hospitalization, change in medical status, etc., the system 302 may analyze the cost profile data 326 to determine if a change is detected. As described above, the system 302 may utilize the reduction value data 314 to determine if the detected change exceeds a certain reduced value in order for the cost profile to be stored in the reduced cost profile data 316.

In embodiments, the memory 308 may store notification(s) data 318 including notification type(s) 336, notification content 338, and user response data 340. For example, the notification types 336 may include one or more types of notifications available for generation and transmission to a user. Examples may include types device notifications, such as text messages, call phones, emails, etc. The notification content 338 may include content to be included in the notification(s) such as links to assist a user in enrolling in a care program, to learn more about the care program, to schedule an appointment for in-person assistance, etc. In addition, the user response data 340 may include data indicating an interaction of the user with the notification, a lack of interaction with the notification, and/or the type of interaction (e.g., selections) associated with each notification, notification type(s) 336, and/or each notification content 338. For example, the user response data 340 may indicate that the user opened the email notification, but did not select any links included. In another example, the user response data 340 may indicate that the user did not open the email at all, and may thus indicate that this type of notification is not effective for this user and/or user's having similar user data associated.

In another embodiment, the memory 308 may store one or more machine learning components 320 including prediction data 342 and learned notification data 344. For example, the machine learning components 320 may implement one or more machine learning algorithms to train one or more indicator model(s), such as indicator model(s) 206 described in FIG. 2, to determine prediction data 342 associated with users that have benefitted from enrollment in the complex care program. For example, the prediction data 342 may include user data 310 and/or one or more combinations of aspects of the user data 310 associated with the users benefiting from enrollment. The system 302 may utilize the prediction data 342 to determine users that may likewise benefit from enrollment in the complex care program, as described herein. For example, the system 302 may receive user data 310 associated with a user that is a candidate for enrollment (e.g., according to the complex care program data 312). The system may compare the user data 310 with the prediction data 342 to determine whether an association exists. If an association exists (e.g., the user data includes data associated with the predicted data 342 determined by the machine learning components 320 as being associated with users that have historically benefitted from enrollment), the system 302 may determine, or predict, that the user will likewise benefit from enrollment.

In addition, the machine learning components 320 may implement one or more machine learning algorithms to determined learned notification data 344 indicating notification types and/or content that user(s) have interacted with and/or that have resulted in engaging the user to enrollment. For example, the machine learning components 320 may determine, based at least in part on the notification data 318 that a certain notification type is more effective than others (e.g., elicits a higher user response and/or causes more users to enroll). In addition, the machine learning components 320 may determine which reminder type and/or content is most effective for a user that is predicted to benefit from enrollment. For example, over time, it may be determined that text message notifications and/or notifications with interactive links cause more users under a certain age to interact with the notification and/or enroll as a result of the text message. Thus, if the predicted user is of the certain age, the system 302 may transmit a text message notification in lieu of an email. The machine learning component(s) 320 may execute any type of supervised learning algorithms (e.g., nearest neighbor, Naïve Bayes, Neural Networks, unsupervised learning algorithms, semi-supervised learning algorithms, reinforcement learning algorithms, and so forth.

As used herein, a processor, such as processor(s) 304, may include multiple processors and/or a processor having multiple cores. Further, the processors may comprise one or more cores of different types. For example, the processors may include application processor units, graphic processing units, and so forth. In one implementation, the processor may comprise a microcontroller and/or a microprocessor. The processor(s) 304 may include a graphics processing unit (GPU), a microprocessor, a digital signal processor or other processing units or components known in the art. Alternatively, or in addition, the functionally described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), etc. Additionally, at least some of the processor(s) 304 may possess its own local memory, which also may store program components, program data, and/or one or more operating systems.

The memory 308 may include volatile and nonvolatile memory, removable and non-removable media implemented in any method or technology for storage of information, such as computer-readable instructions, data structures, program component, or other data. Such memory 308 includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, RAID storage systems, or any other medium which can be used to store the desired information and which can be accessed by a computing device. The memory 308 may be implemented as computer-readable storage media ("CRSM"), which may be any available physical media accessible by the processor(s) 304 to execute instructions stored on the memory 308. In one basic implementation, CRSM may include random access memory ("RAM") and Flash memory. In other implementations, CRSM may include, but is not limited to, read-only memory ("ROM"), electrically erasable programmable read-only memory ("EEPROM"), or any other tangible medium which can be used to store the desired information and which can be accessed by the processor(s).

Further, functional components may be stored in the respective memories, or the same functionality may alternatively be implemented in hardware, firmware, application specific integrated circuits, field programmable gate arrays, or as a system on a chip (SoC). In addition, while not illustrated, each respective memory, such as memory 308, discussed herein may include at least one operating system (OS) component that is configured to manage hardware resource devices such as the network interface(s), the I/O devices of the respective apparatuses, and so forth, and provide various services to applications or components executing on the processors. Such OS component may implement a variant of the FreeBSD® operating system as promulgated by the FreeBSD Project; other UNIX® or UNIX-like variants; a variation of the Linux® operating system as promulgated by Linus Torvalds; the FireOS operating system from Amazon.com Inc. of Seattle, Washington, USA; the Windows® operating system from Microsoft Corporation of Redmond, Washington, USA; LynxOS® as promulgated by Lynx® Software Technologies, Inc. of San Jose, California; Operating System Embedded (Enea® OSE) as promulgated by ENEAR AB of Sweden; and so forth.

The network interface(s) 306 may enable communications between the components and/or devices and/or with one or more other remote systems, as well as other networked devices. Such network interface(s) 306 may include one or more network interface controllers (NICs) or other types of transceiver devices to send and receive communications over a network.

For instance, at least some of the network interface(s) 306 may include a personal area network (PAN) component to enable communications over one or more short-range wireless communication channels. For instance, the PAN component may enable communications compliant with at least one of the following standards IEEE 802.15.4 (ZigBee®), IEEE 802.15.1 (Bluetooth®), IEEE 802.11 (WiFi), or any other PAN communication protocol. Furthermore, at least some of the network interface(s) 306 may include a wide area network (WAN) component to enable communication over a wide area network.

Figure 4:
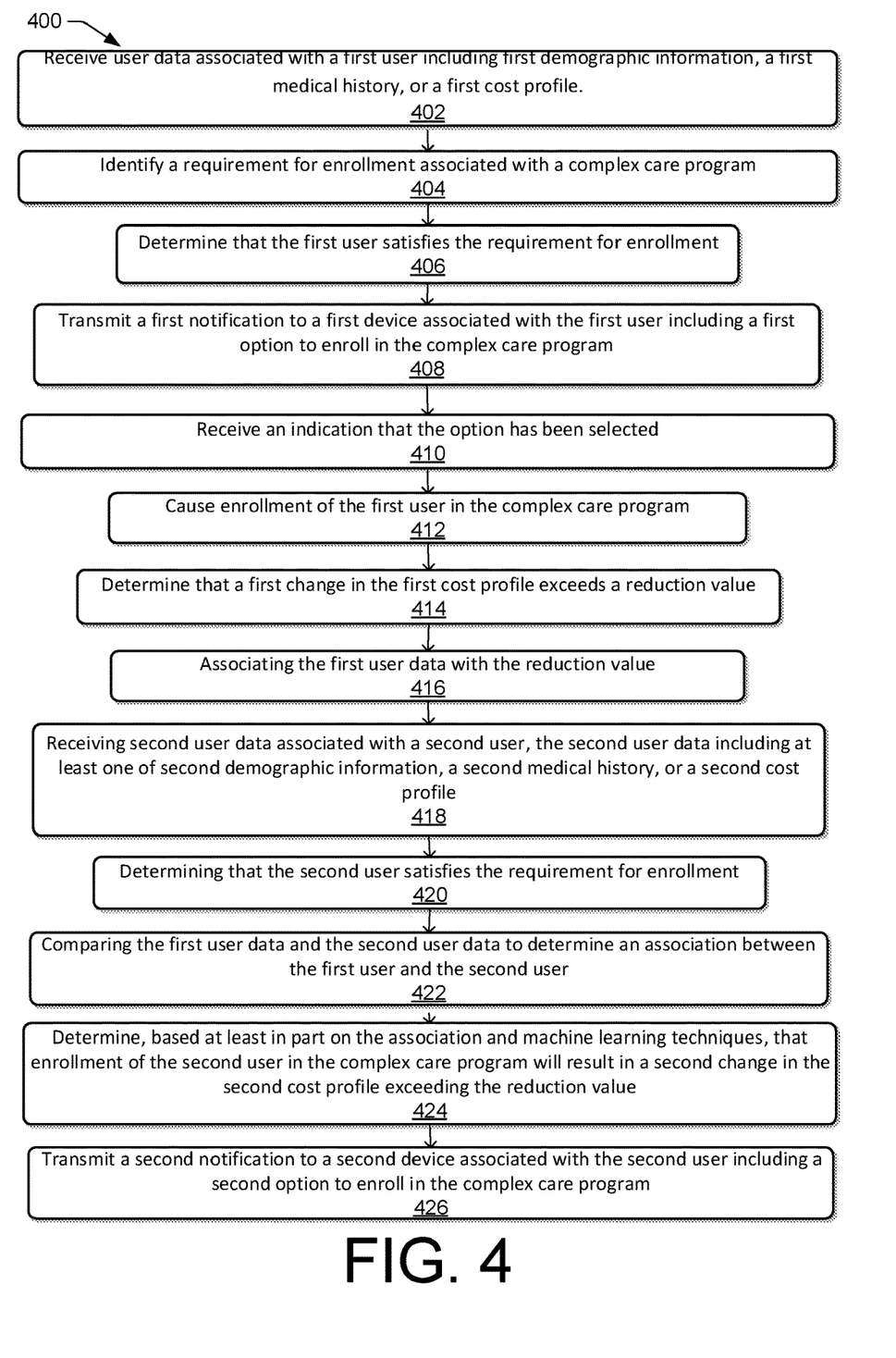
FIGS. 4 and 5 illustrate various flow diagrams of example processes for complex care tools.
Figure 5:
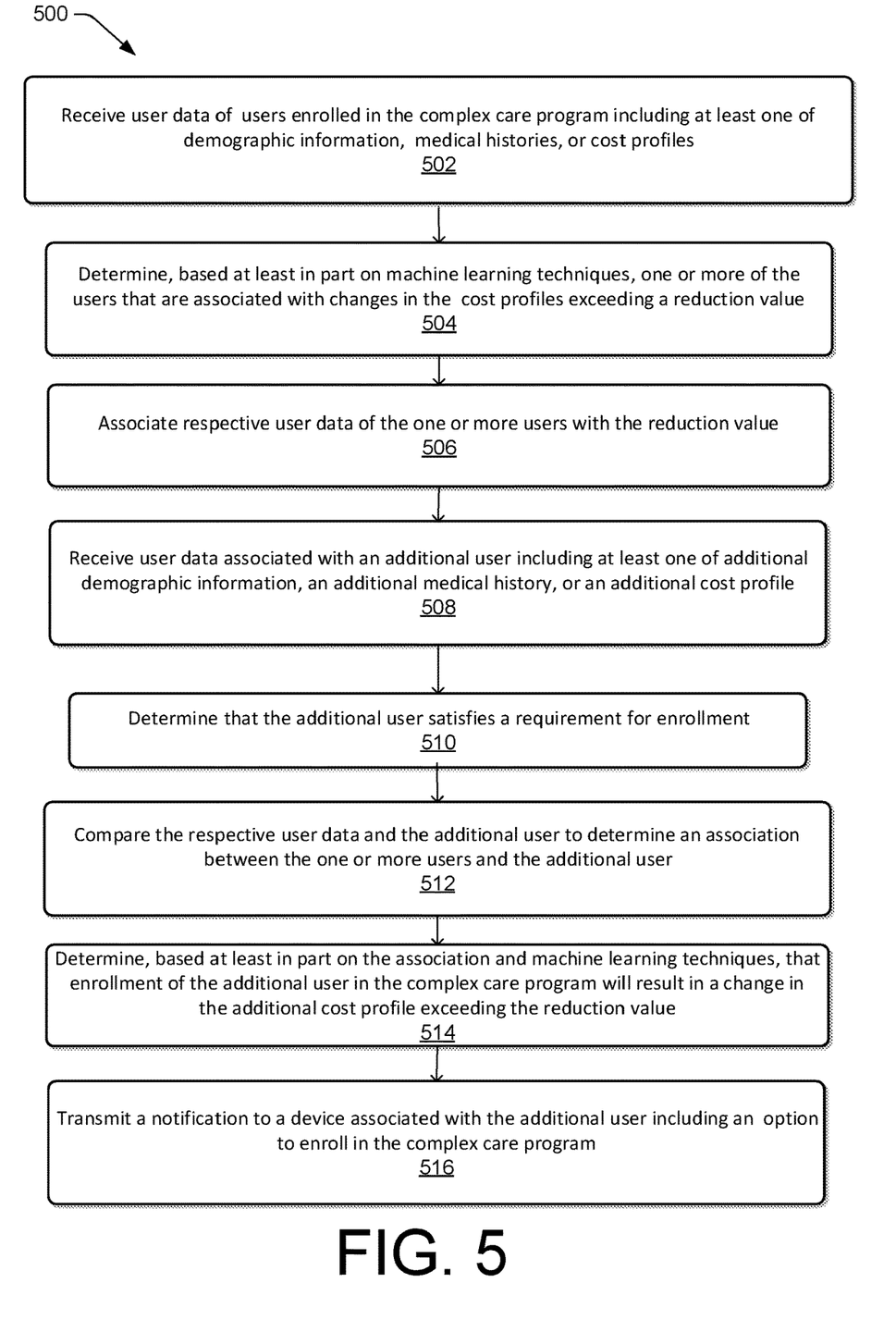

FIGS. 4 and 5 illustrate various flow diagrams of example processes for the complex care tools. The processes described herein are illustrated as collections of blocks in logical flow diagrams, which represent a sequence of operations, some or all of which may be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation, unless specifically noted. Any number of the described blocks may be combined in any order and/or in parallel to implement the process, or alternative processes, and not all of the blocks need be executed. For discussion purposes, the processes are described with reference to the environments, architectures and systems described in the examples herein, such as, for example those described with respect to FIGS. 1-3, although the processes may be implemented in a wide variety of other environments, architectures, and systems.

FIG. 4 illustrates a flow diagram of an example process 400 for complex care tools. The order in which the operations or steps are described is not intended to be construed as a limitation, and any number of the described operations may be combined in any order and/or in parallel to implement process 400.

At block 402, the process 400 may include receiving user information including user data associated with a first user and including first demographic information, a first medical history, or a first cost profile. For example, the systems for complex care tools described herein may receive and/or access user data including demographic information, a medical history, and/or a cost profile. The demographic information data may include basic information such as age, gender, race, etc. and/or basic identifying information such as a legal name, social security number, etc. The medical history data may include information such as physician records, lab results, hospitalization records, prescribed medications, etc.

At block 404, the process 400 may include identifying a requirement for enrollment associated with a complex care program. For example, the system may identify one or more requirements to determine if a user is a candidate for enrollment in the complex care program. The requirements may include eligibility requirements such as age, gender, medical conditions, etc. The system may analyze the user data, received at block 406, to determine if the first user data indicates that the first user is a candidate for enrollment in the complex care program.

At block 406, the process 400 may include determining that the first user satisfies the requirement for enrollment. For example, the system may analyze the user data, received at block 402, and the program requirements, identified at block 404, to determine that the first user satisfies the requirement for enrollment and is therefore a candidate for enrollment in the complex care program.

At block 408, the process 400 may include transmitting a first notification to a first device associated with the first user, including a first option to enroll in the complex care program. For example, in response to determining that the first user satisfies the requirement for enrollment, the system may transmit a notification to a first device associated with the first user. The notification may include a first option to enroll in the complex care program. For example, the notification may cause the user device to initiate an application residing on the device and cause the option to be displayed. The option may include a selectable element, such as a link or interface button, that allows the user to enroll in the complex care program, obtain additional information regarding the complex care program, schedule an appointment for an enrollment consultation, etc.

At block 410, the process 400 may include receiving an indication that the option has been selected. For example, the system may receive an indication that the option included in the notification transmitted at block 408 has been selected by the first user. The indication may also include additional details about the selection and/or the first user's interaction with the content of the notification.

At block 412, the process 400 may include causing enrollment of the first user in the complex care program. For example, in response to receiving the indication at block 410, the system may cause the first user to be enrolled in the complex care program. For instance, having received the indication that the first user has selected the option to be enrolled in the complex care program, the system may utilize the user's data (e.g., the user data received at block 402 and/or user information provided upon enrollment) to enroll the user in the complex care program.

At block 414, the process 400 may include determining that a first change in the first cost profile exceeds a reduction value. For example, the system may receive a predetermined reduction value and/or determine a reduction value based on machine learning techniques. The reduction value may indicate a value by which the cost profile must be reduced to achieve the intended benefit of the complex care program. For example, the reduction value may indicate that the cost profile must be reduced by at least 40% to determine that enrollment in the complex care program has been benefit to the first user. The system may utilize this reduction value to determine that a first change in the first cost profile exceeds the reduction value. For example, after the user has been enrolled in the complex care program, the system may monitor the cost profile for changes and/or determine a second cost profile value in response to a triggering event (e.g., the user being admitted to the hospital, a change in a medical condition, a change in resource utilization, etc.). The system may determine if the change in the cost profile, and/or if the change between the first cost profile value and the second cost profile value, exceeds the reduction value.

At block 416, the process 400 may include associating the first user data with the reduction value. For example, in response to determining, at block 414, that the first change in the first cost profile exceeds the reduction value, the system may associate the first user data with the reduction value. In this way, the system may utilize the first user data to predict, utilizing machine learning techniques, that an additional user would likewise benefit from enrollment in the complex care program.

At block 418, the process 400 may include receiving second user data associated with a second user, the second user data including at least one of second demographic information, a second medical history, or a second cost profile. For example, the system may receive and/or access second user data associated with the second user.

At block 420, the process 400 may include determining that the second user satisfies the requirement for enrollment. For example, the system may utilize the complex care program requirements, identified at block 404, to determine that the second user is a candidate for enrollment in the complex care program.

At block 422, the process 400 may include comparing the first user data and the second user data to determine an association between the first user and the second user. For example, the system may compare the first user data and the second user data to determine an overlap in characteristics and/or data values associated with the user data (e.g., that the users are in the same age group, have a similar disease status, etc.).

At block 424, the process 400 may include determining, based at least in part on the association and machine learning techniques, that enrollment of the second user in the complex care program will result in a second change in the second cost profile exceeding the reduction value. For example, based on the association determined at block 422, along with machine learning techniques, the system may determine (e.g., predict) that the second user will benefit from enrollment in the complex care program. For example, based on the association and/or machine learning models utilizing historical data, the system may predict that the cost profile associated with the second user will be reduced by a value exceeding that of the reduction value as a result of enrollment. In this way, the system may utilize user data from users who have benefitted from enrollment to predict that additional users will likewise benefit from enrollment.

At block 426, the process 400 may include transmitting a second notification to a second device associated with the second user including a second option to enroll in the complex care program. For example, in response to determining, at block 424, that the second user will benefit from enrollment, the system may transmit a notification to a second device associated with the second user. The notification may include an option to enroll in the complex care program. For example, the notification may cause the second user device to initiate an application residing on the device and cause the option to be displayed. The option may include a selectable element, such as a link or interface button, that allows the second user to enroll in the complex care program, obtain additional information regarding the complex care program, schedule an appointment for an enrollment consultation, etc.

FIG. 5 illustrates a flow diagram of another example process 500 for complex care tools. The order in which the operations or steps are described is not intended to be construed as a limitation, and any number of the described operations may be combined in any order and/or in parallel to implement process 500.

At block 502, the process 500 may include receiving user data of users enrolled in the complex care program including at least one of demographic information, medical histories, or cost profiles. For example, the system may receive user data associated with one or more users that are already enrolled in the complex care program.

At block 504, the process 500 may include determining, based on machine learning one or more of the users that are associated with changes in the cost profiles exceeding a reduction value. For example, the system may determine, based on machine learning techniques and utilizing the user data and/or historical data associated with the users, that one or more users have experienced changes in associated cost profiles that exceed a reduction value. The reduction value, as described herein, may include a predetermined value and/or a value determined by the machine learning techniques.

At block 506, the process 500 may include associating respective user data of the one or more users with the reduction value. For example, in response to determining, at block 504, that the one or more users are associated with changes in the cost profiles exceeding the reduction value, the system may associate the respective user data of those users with the reduction value. In this way, the system may utilize the respective user data to predict, utilizing machine learning techniques, that an additional user would likewise benefit from enrollment in the complex care program.

At block 508, the process 500 may include receiving additional user data associated with an additional user including at least one of additional demographic information, an additional medical history, or an additional cost profile. For example, the system may receive and/or access additional user data associated with the additional user.

At block 510, the process 500 may include determining that the additional user satisfies the requirement for enrollment. For example, the system may identify and/or access requirements associated with enrollment in the complex care program. For example, the system may analyze the additional user data, received at block 508, and program requirements (such as those identified at block 404) to determine that the additional user satisfies the requirement for enrollment and is therefore a candidate for enrollment in the complex care program.

At block 512, the process 500 may include comparing the respective user data and the additional user data to determine an association between the one or more users and the additional user. For example, the system may compare the respective user data and the additional user data to determine an overlap in characteristics and/or data values (e.g., that the one or more users and the additional user are in the same age group, have a similar disease status, etc.).

At block 514, the process 500 may include determining, based at least in part on the association and machine learning techniques, that enrollment of the additional user in the complex care program will result in a change in the additional cost profile exceeding the reduction value. For example, the system may determine (e.g., predict), using the association determined at block 512 and machine learning techniques, that the additional user will benefit from enrollment in the complex care program. That is, the system may predict that the additional user will experience a similar reduction in an associated cost profile (e.g., exceeding the reduction value), as that of the one or more users. In this way, the system may utilize user data from the one or more users who have benefitted from enrollment to predict that additional users will likewise benefit from enrollment.

At block 516, the process 500 may include transmitting a notification to a device associated with the additional user including an option to enroll in the complex care program. For example, in response to determining, at block 514, that the additional user will benefit from enrollment, the system may transmit a notification to a device associated with the additional user. The notification may include an option to enroll in the complex care program. For example, the notification may cause the user device to initiate an application residing on the device and cause the option to be displayed. The option may include a selectable element, such as a link or interface button, that allows the second user to enroll in the complex care program, obtain additional information regarding the complex care program, schedule an appointment for an enrollment consultation, etc.

While the foregoing invention is described with respect to the specific examples, it is to be understood that the scope of the invention is not limited to these specific examples. Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Although the application describes embodiments having specific structural features and/or methodological acts, it is to be understood that the claims are not necessarily limited to the specific features or acts described. Rather, the specific features and acts are merely illustrative some embodiments that fall within the scope of the claims of the application.

What is claimed is:

1. A method comprising:
receiving first user data associated with a first user, the first user data including at least a medical history of the first user and a first cost profile indicating healthcare expenses associated with the first user;
receiving first data associated with a program, the first data including at least requirements for the program;
based at least in part on the first user data and the first data, causing the first user to be enrolled in the program;
receiving second data associated with reduced healthcare expenses of the first user due to enrollment into the program;
generating a first machine learning model configured to identify users whose healthcare expenses would be reduced below a threshold reduction value if enrolled in the program;
generating a first training dataset indicating outcomes of the first machine learning model when identifying users whose healthcare expenses would be reduced below a threshold reduction value if enrolled in the program, wherein the first user data, the first data, and the second data are altered to generate the first training dataset formatted as first input data to be utilized by the first machine learning model;
generating a first trained machine learning model based at least in part on training the first machine learning model utilizing the first training dataset
receiving second user data associated with second users, the second user data including at least medical histories of individual ones of the second users and second cost profiles indicating healthcare expenses associated with the individual ones of the second users;
determining, based at least in part on inputting the second user data into the first trained machine learning model, that enrollment of a second user of the second users in the program will reduce a second user's healthcare expenses below the threshold reduction value;
identifying third data associated with notification data for the second user, notification data including at least one notification preference;
identifying fourth data associated with response data for the second user, the response data including at least a response history of the second user;
generating a second machine learning model configured to determine notification types most likely to lead to acceptance by the users;
generating a second training dataset indicating outcomes of the second machine learning model when determining the notification types most likely to lead to acceptance by the users wherein the third data and the fourth data are altered to generate the second training dataset formatted as second input data to be utilized by the second machine learning model;
generating a second trained machine learning model based at least in part on training the second machine learning model utilizing the second training dataset;
determining, based at least in part on inputting the third data and the fourth data into the second trained machine learning model, a type of notification most likely to lead to acceptance by the second user; and transmitting, based at least in part on determining that enrollment of the second user will reduce the second user's healthcare expenses below the threshold reduction value, the type of notification most likely to lead to acceptance by the second user including an option to enroll in the program.

2. The method of claim 1, wherein the at least requirements for the program include at least one of an age requirement, a gender requirement, a disease status requirement, or a resource utilization requirement.

3. The method of claim 1, further comprising generating the first training dataset utilizing additional user data of additional users enrolled in the program, the additional user data including at least one of demographic information, medical histories, or additional cost profiles indicative of healthcare expenses associated with the additional users, wherein the healthcare expenses associated with the additional users were reduced below the threshold reduction value based at least in part on enrolling in the program.

4. The method of claim 1, wherein the first user data further includes first medical history information associated with the first user, and wherein the determining, based at least in part on inputting the second user data into the first trained machine learning model, that enrollment of the second user in the program will reduce the second user's healthcare expenses below the threshold reduction value is based at least in part on a correlation between the first medical history information and second medical history information associated with the second user.

5. The method of claim 1, wherein the first user data further includes first demographic information associated with the first user, and wherein the determining, by the first machine learning model, that enrollment of the second user in the program will reduce the second user's healthcare expenses below the threshold reduction value is based at least in part on a correlation between the first demographic information and second demographic information associated with the second user.

6. The method of claim 1, the second user data further including at least second demographic information, second medical history information, and a second cost profile, wherein the determining, utilizing the first machine learning model, that enrollment of the second user in the program will reduce the second user's healthcare expenses below the threshold reduction value comprises inputting the second user data into the first machine learning model.

7. The method of claim 1, further comprising refraining from offering, to a third user, an opportunity to enroll in the program based at least in part on a determination, utilizing the first machine learning model, that enrollment of the third user in the program would fail to reduce a third user's healthcare expenses below the threshold reduction value.

8. The method of claim 1, wherein determining that enrolling the first user in the program reduced the healthcare expenses associated with the first user below the threshold reduction value is based at least in part on monitoring the first cost profile subsequent to enrolling the first user in the program.

9. A system comprising:
one or more processors; and
one or more non-transitory computer-readable media storing instructions that, when executed, cause the one or more processors to perform operations comprising:
receiving first user data associated with a first user, the first user data including at least first demographic information, first medical history information, and first cost profile information indicative of healthcare expenses associated with the first user;
receiving first data, the first data including at least requirements for enrollment in a complex care program;
determining, based at least in part on the first user data, that the first user satisfies the at least requirements for enrollment;
transmitting, based at least in part on the first user satisfying the at least requirements, a first notification to a first device associated with the first user, the first notification indicating a first option to enroll in the complex care program;
based at least in part on receiving an indication that the first option has been selected, causing enrollment of the first user in the complex care program;
determining, based at least in part on monitoring the first cost profile information, that the enrollment of the first user in the complex care program reduced the healthcare expenses associated with the first user below a threshold reduction value;
generating a first machine learning model configured to predict whether enrollment of users in the complex care program will reduce healthcare expenses associated with the users below the threshold reduction value;
generating a first training dataset indicating outcomes of the first machine learning model when predicting whether enrollment of users in the complex care program will reduce healthcare expenses associated with the users below the threshold reduction value, wherein the first user data and the first data are altered to generate the first training dataset formatted as input data to be utilized by the first machine learning model;
generating a first trained machine learning model based at least in part on training the first machine learning model utilizing the first training dataset;
receiving second user data associated with a second user, the second user data including at least second demographic information, a second medical history information, and a second cost profile, the second cost profile indicative of healthcare expenses associated with the second user;
determining, based at least in part on inputting the second user data into the first trained machine learning model, that enrollment of the second user in the complex care program will reduce the healthcare expenses associated with the second user below the threshold reduction value;
identifying second data associated with notification data for the second user, notification data including at least one notification preference;
identifying third data associated with response data for the second user, the response data including at least a response history of the second user;
generating a second machine learning model configured to determine notification types most likely to lead to acceptance by the users;
generating a second training dataset indicating outcomes of the second machine learning model when determining the notification types most likely to lead to acceptance by the users wherein the second data and the third data are altered to generate the second training dataset formatted as second input data to be utilized by the second machine learning model;
generating a second trained machine learning model based at least in part on training the second machine learning model utilizing the second training dataset;

determining, based at least in part on inputting the second data and the third data into the second trained machine learning model, a type of notification most likely to lead to acceptance by the second user based at least in part on determining that enrollment of the second user in the complex care program will reduce the healthcare expenses associated with the second user below the threshold reduction value, sending the type of notification most likely to lead to acceptance by the second user including a second option to enroll in the complex care program.

10. The system of claim 9, wherein the at least requirements for enrollment associated with the complex care program is at least one of an age requirement, gender requirement, disease status requirement, or resource utilization requirement.

11. The system of claim 9, wherein generating the first training dataset utilizing additional user data of additional users enrolled in the complex care program, the additional user data including at least one of additional demographic information, additional medical histories, and additional cost profiles indicative of healthcare expenses associated with the additional users, wherein the healthcare expenses associated with the additional users were reduced below the threshold reduction value based at least in part on enrolling in the complex care program.

12. The system of claim 9, wherein the determining, based at least in part on inputting the second user data into the first trained machine learning model, that enrollment of the second user in the complex care program will reduce the healthcare expenses associated with the second user below the threshold reduction value is based at least in part on a correlation between the first medical history information and the second medical history information.

13. The system of claim 9, wherein the determining, based at least in part on inputting the second user data into the first trained machine learning model, that enrollment of the second user in the complex care program will reduce the healthcare expenses associated with the second user below the threshold reduction value is based at least in part on a correlation between the at least first demographic information and the at least second demographic information.

14. The system of claim 9, the operations further comprising refraining from offering, to a third user, an opportunity to enroll in the complex care program based at least in part on a determination, utilizing the first machine learning model, that enrollment of the third user in the complex care program would fail to reduce a third user's healthcare expenses below the threshold reduction value.

15. One or more non-transitory computer-readable media storing instructions that, when executed, cause one or more processors to perform operations comprising:

receiving first user data associated with a first user, the first user data including at least first demographic information, first medical history information, and first cost profile information indicative of healthcare expenses associated with the first user;

receiving first data, the first data including at least requirements for enrollment in a complex care program;

determining, based at least in part on the first user data, that the first user satisfies the at least requirements for enrollment;

transmitting, based at least in part on the first user satisfying the at least requirements, a first notification to a first device associated with the first user, the first notification indicating a first option to enroll in the complex care program;

based at least in part on receiving an indication that the first option has been selected, causing enrollment of the first user in the complex care program;

determining, based at least in part on monitoring the first cost profile information, that the enrollment of the first user in the complex care program reduced the healthcare expenses associated with the first user below a threshold reduction value;

generating a first machine learning model configured to predict whether enrollment of users in the complex care program will reduce healthcare expenses associated with the users below the threshold reduction value;

generating a first training dataset indicating outcomes of the first machine learning model when predicting whether enrollment of users in the complex care program will reduce healthcare expenses associated with the users below the threshold reduction value, wherein the first user data and the first data are altered to generate the first training dataset formatted as input data to be utilized by the first machine learning model;

generating a first trained machine learning model based at least in part on training the first machine learning model utilizing the first training dataset;

receiving second user data associated with a second user, the second user data including at least second demographic information, a second medical history information, and a second cost profile, the second cost profile indicative of healthcare expenses associated with the second user;

determining, based at least in part on inputting the second user data into the first trained machine learning model, that enrollment of the second user in the complex care program will reduce the healthcare expenses associated with the second user below the threshold reduction value;

identifying second data associated with notification data for the second user, notification data including at least one notification preference;

identifying third data associated with response data for the second user, the response data including at least a response history of the second user;

generating a second machine learning model configured to determine notification types most likely to lead to acceptance by the users;

generating a second training dataset indicating outcomes of the second machine learning model when determining the notification types most likely to lead to acceptance by the users wherein the second data and the third data are altered to generate the second training dataset formatted as second input data to be utilized by the second machine learning model;

generating a second trained machine learning model based at least in part on training the second machine learning model utilizing the second training dataset;

determining, based at least in part on inputting the second data and the third data into the second trained machine learning model, a type of notification most likely to lead to acceptance by the second user and based at least in part on determining that enrollment of the second user in the complex care program will reduce the healthcare expenses associated with the second user below the threshold reduction value, sending the type of notification most likely to lead to acceptance by the second user including a second option to enroll in the complex care program.

16. The one or more non-transitory computer-readable media of claim 15, wherein the at least requirements for enrollment associated with the complex care program is at least one of an age requirement, gender requirement, disease status requirement, or resource utilization requirement.

17. The one or more non-transitory computer-readable media of claim 15, wherein generating the first training dataset utilizing additional user data of additional users enrolled in the complex care program, the additional user data including at least one of additional demographic information, additional medical histories, and additional cost profiles indicative of healthcare expenses associated with the additional users, wherein the healthcare expenses associated with the additional users were reduced below the threshold reduction value based at least in part on enrolling in the complex care program.

18. The one or more non-transitory computer-readable media of claim 15, wherein the determining, based at least in part on inputting the second user data into the first trained machine learning model, that enrollment of the second user in the complex care program will reduce the healthcare expenses associated with the second user below the threshold reduction value is based at least in part on a correlation between the first medical history information and the second medical history information.

19. The one or more non-transitory computer-readable media of claim 15, wherein the determining, based at least in part on inputting the second user data into the first trained machine learning model, that enrollment of the second user in the complex care program will reduce the healthcare expenses associated with the second user below the threshold reduction value is based at least in part on a correlation between the at least first demographic information and the at least second demographic information.

20. The one or more non-transitory computer-readable media of claim 15, the operations further comprising refraining from offering, to a third user, an opportunity to enroll in the complex care program based at least in part on a determination, utilizing the first machine learning model, that enrollment of the third user in the complex care program would fail to reduce a third user's healthcare expenses below the threshold reduction value.

\* \* \* \* \*